United States Patent [19]

Klobucar et al.

[11] Patent Number: 5,073,284

[45] Date of Patent: Dec. 17, 1991

[54] PHOSPHONITRILIC MIXED ESTERS

[75] Inventors: W. Dirk Klobucar; Charles H. Kolich, both of Baton Rouge, La.

[73] Assignee: Ethyl Corporation, Richmond, Va.

[21] Appl. No.: 624,877

[22] Filed: Dec. 5, 1990

Related U.S. Application Data

[63] Continuation-in-part of Ser. No. 447,553, Dec. 7, 1989, abandoned.

[51] Int. Cl.$^5$ ............... C10M 105/70; C10M 105/74
[52] U.S. Cl. ............................. 252/78.5; 252/49.9; 558/80; 558/157
[58] Field of Search ............... 252/78.5, 49.9; 558/80, 558/157

[56] References Cited

U.S. PATENT DOCUMENTS 4,698,439 10/1987 Kolich et al. .................. 558/80
4,724,264 2/1988 Nakacho et al. ................ 558/80

FOREIGN PATENT DOCUMENTS 0145002 6/1985 European Pat. Off. .

OTHER PUBLICATIONS

Singler, et al., Ind. Eng. Chem. (Prod. Res. & Dev.), vol. 25, No. 1 (1986) pp. 46–57.
Lederle, et al., *J. Chem & Eng. Data*, vol. 11, No. 2, Apr. 1966, p. 221.
Ottmann, et al., Ind. & Eng. Chem. (Prod. Res. & Dev.), vol. 5, No. 2, Jun. 1966, p. 202.

*Primary Examiner*—Paul Lieberman
*Assistant Examiner*—Christine A. Skane
*Attorney, Agent, or Firm*—Richard J. Hammond

[57] ABSTRACT

A hydraulic fluid that remains solids-free at temperatures as low as about $-30°$ C. and has a pour point as low as about $-42°$ C. comprises a cyclic phosphazene oligomer mixture, the structural formula of each molecule of which contains 3 or 4 units selected at random from the group consisting of

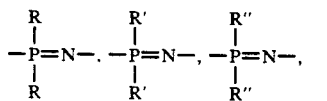

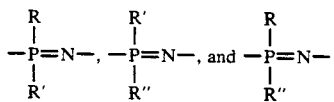

wherein R is a fluoroalkoxy group $-OCH_2(CF_2)_mCF_2Z$, where Z is hydrogen or fluorine, and m is 0 or an integer from 1 to 10; R' and R" are different alkoxyalkyloxy groups in which linear or branched $C_{1-12}$ alkoxy is substituted with linear or branched $C_{1-12}$ alkoxy with the proviso that all of R, R' and R" are present in the oligomer mixture.

10 Claims, No Drawings

PHOSPHONITRILIC MIXED ESTERS

This is a continuation-in-part of application Ser. No. 07/447,553 filed Dec. 7, 1989.

This invention relates to novel fluoroalkoxy phosphazenes. More particularly, this invention relates to hydraulic fluids having excellent low temperature properties comprising alkoxy and fluoroalkoxy substituted phosphazenes.

BACKGROUND OF THE INVENTION

Phosphazenes are chemical compounds containing the following structural unit in which the free valences can be occupied by various groups.

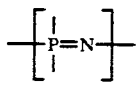

A variety of phosphazene compositions and methods of preparation are known in the art. U.S. Pat No. 3,291,865 to Kober, et al. discloses non-flammable, hydrolytically stable phosphazene compositions for use as hydraulic fluids, lubricants and additives. These phosphazenes carry an aryloxy and a fluoroalkoxy substituent and are synthesized by forming the alkali metal salt of the fluorinated alcohol followed by reaction of that salt and a phenolic salt with a phosphonitrilic chloride.

Lederle, et al, J. Chem. & Eng. Data, Vol. 11, No. 2, April 1966, page 221 discloses fire resistant hydraulic fluids made in a manner similar to Kober et al. Ottmann et al, Ind. & Eng. (Chem. Prod. Res. & Dev.), Vol. 5, No. 2, June 1966, page 202 describe arylamino fluoroalkoxy-substituted phosphonitrilic cyclic trimers.

Singler et al, "Army Science Conference Paper", A117298 sets forth the synthesis and evaluation of phosphazene fluids in an attempt to find a replacement for triarylphosphates under military specification MIL-H-19457c. This research involved the use of trifluoroethoxy-substituted cyclic phosphonitrilates which were also substituted with either m-chlorophenoxy or m-trifluoromethylphenoxy groups.

Singler, "Potential of Phosphazenes as Hydraulic Fluids", Hydraulic Fluids Meeting, NASA Ames Research Center, February 1976 summarizes the effect of various substituents on the substituted cyclic phosphonitrilic trimers and tetramers.

More recently, Singler et al, Ind. Eng. Chem. (Prod. Res. & Dev.), Vol. 25, No. 1 (1986) describe hydraulic fluids made by substituting cyclic phosphonitrilic chloride with both aryloxy groups and trifluoroethoxy groups.

Carr, Eur. Pat. Appl. No. 0 145 002, published June 19, 1985 discloses a phosphazene fluid prepared by reacting cyclic phosphonitrilic chloride trimer with a phenol, a fluoroalcohol or mixtures thereof.

Fluoroalkoxy-substituted phosphazenes also are disclosed in U.S. Pat. No. 3,304,350 to Kober, et al. These highly fluorinated materials have a high flash point and display acceptable low-temperature properties in hydraulic fluid applications. A variety of other phosphazene compositions are known in the art. U.S. Pat. No. 3,370,020 to Allcock, et al, U.S. Pat. No. 3,505,087 to Godfrey, U.S. Pat. No. 4,081,593 to Lanier, U.S. Pat No. 4,018,967 to Roller, et al. U.S. Pat. Nos. 4,110,421, 4,157,425 and 4,116,891 to Dieck, et al, U.S. Pat. No. 3,990,900 to Franko Filipasic, et al and U.S. Pat. No. 3,545,942 to Rice, et al disclose phosphazenes which may be substituted by a variety of alkoxy, arylalkoxy or aryloxy groups.

Most recently we have disclosed in U.S. Pat. No. 4,698,439 a method for preparing phosphazene hydraulic fluids that remain solids-free on storage at temperatures down to −30° C. These materials have fluoroalkoxy as well as substituted and unsubstituted aryloxy substituents on the phosphonitrilic backbone.

While many of the prior art phosphazene fluids are fire resistant, having a relatively high flash point, unacceptable low temperature properties restrict their utility. Further, because of the high concentrations of fluorine required, the cost of the resulting phosphazene hydraulic fluid is very high when compared to conventional fluids.

SUMMARY OF THE INVENTION

It is an objective of the present invention to provide phosphazene hydraulic fluids that exhibit a pour point as low as about −42° C. and remain solids-free at temperatures as low as about −30° C.

It is a further object of the present invention to provide a phosphazene hydraulic fluid that has a flash point higher than about 200° C.

It is an additional object of the present invention to provide a phosphazene hydraulic fluid that has less fluorine content than the prior art hydraulic fluids with comparable properties.

These and other objects of the present invention will become apparent from the following more detailed description of the invention.

The aforesaid objectives have been achieved with a hydraulic fluid which comprises a cyclic phosphazene oligomer mixture, the structural formula of each molecule of which contains 3 or 4 units linked together in a ring and selected at random from the group consisting of

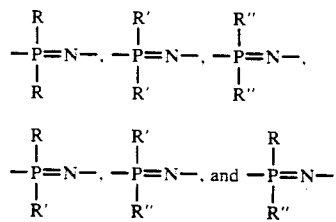

wherein R is a fluoroalkoxy group $-OCH_2(CF_2)_mCF_2Z$, where Z is hydrogen or fluorine, and m is 0 or an integer from 1 to 10; R' and R" preferably are different alkoxyalkyloxy groups in which linear or branched $C_{1-12}$ alkoxy is substituted with linear or branched $C_{1-12}$ alkoxy; with the proviso that all of R, R' and R" are present in the oligomer mixture.

DETAILED DESCRIPTION

The present invention provides low molecular weight cyclic phosphonitrilic oligomers having fluoroalkoxy substituents (R) and two different alkoxyalkyloxy substituents (R' and R").

These substituents appear on the individual units which make up the 3 or 4 unit oligomers as shown in the 6 structural formulae which appear above. Since the units which appear in the individual 3 unit or 4 unit oligomer molecules are randomly selected from the 6 units shown above, it will be evident that the phosphazene oligomers of this invention are mixtures. This is a consequence of the manner in which they are made as will become evident hereinafter.

Suffice it to state that the 3 unit and 4 unit cyclic phosphazene oligomers of this invention are represented by the following structural formulae, the free valences being occupied by the groups R, R' and R".

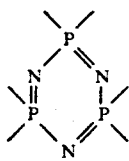 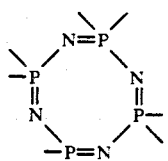

3 unit oligomer     4 unit oligomer

The hydraulic fluid of this invention can comprise cyclic phosphazene oligomers wherein substantially all of the oligomers contain 3 units, wherein substantially all of the oligomers contain 4 units, or wherein a fraction of the oligomers contain 3 units and the remainder contain 4 units. This control is readily achieved by selecting the phosphazene starting material from which the hydraulic fluid is made.

The fluoroalkoxy substituents (R) on the phosphazene oligomers are of the formula $-OCH_2(CF_2)_mCF_2Z$ where Z is hydrogen or fluorine and m is 0 or an integer from 1 to 10. These linear, unbranched substituents range from the simplest, i.e., 2,2,2-trifluoroethoxy, where Z is fluorine and m is 0, to the most complex, 2,2,3,3,4,4,5,5,6,6,7,7,8,8,9,9,10,10,11,11,-12,12,12-tricosafluorododecyloxy, where Z is fluoro and m is 10. Other exemplary fluoroalkoxy substitutents are 2,2-difluoroethoxy, where Z is hydrogen and m is 0, 2,2,3,3-tetrafluoropropoxy, and the like. The preferred fluoroalkoxy substituents are those where m is 0, 1, 2 or 3 and Z is fluorine. Most preferred is the trifluoroethoxy substituent, i.e., m is O and Z is fluorine.

The remaining substituents (R' and R") on the phosphazene oligomers are those termed alkoxyalkyloxy, i.e., substituents of the formula (alkoxy)(alkyl)O—

The alkoxy portion of these substituents is $C_1$ to $C_{12}$ linear or branched alkoxy, e.g., methoxy, ethoxy, isopropoxy, 2-ethyl-1-butoxy, lauryloxy, etc. The alkyl portion of these substituents is linear or branched $C_1$ to $C_{12}$ alkyl, e.g., methyl, ethyl, propyl, isopropyl, etc. The most preferred R' and R" substituents are 2-methoxyethoxy and 1-methoxy-2-propoxy.

Another requirement of this invention is that the cyclic phosphazene oligomer mixture preferably contains two different alkoxyalkyloxy substituents; that is R' and R" preferably are different and both present in the oligomer mixture. In general, it is preferred that the molar amount of fluoroalkoxy substituent R be greater than the molar amounts of either R' or R".

The phosphazene oligomers of the present invention can be prepared by reacting a cyclic phosphonitrilic halide or mixture of phosphonitrile halides, e.g., hexahalocyclotriphosphazene and/or octahalocyclotetraphosphazene, with alkali metal alkoxide to effect substantially complete substitution of the haloge atoms by alkoxy groups. This reaction requires 6 moles of alkoxide for every mole of hexahalocyclotriphosphazene and 8 moles for every mole of octahalocyclotetraphosphazene.

The preparation of the alkali metal alkoxides i.e., RM, R'M and R"M, is well known and occurs by the reaction of an alkali metal with the corresponding alcohol. That is, the sodium salts (the preferred salts) of a mixture of a fluoro-alkanol and two different alkoxyalkanols is produced. In a second step, it is preferred that a slight molar deficiency of the above mixture is then reacted with the phosphonitrilic halide. Then in a third step, additional sodium fluoroalkoxide is added to the reaction mixture to effect complete substitution of all remaining halogen atoms attached to the phosphonitrilic moiety.

Sufficient alkali metal alkoxide and fluoroalkoxide is employed to provide at least the stoichiometric amount required to react with all of the halogen atoms attached to the phosphonitrilic moiety and preferably between about 1.01 and about 1.10 times the stoichiometric amount.

The reaction may be carried out in an inert solvent capable of dissolving the phosphonitrilic halide. Suitable solvents include benzene, toluene, xylene, chlorobenzene, cyclohexane, tetrahydrofuran, 1,4-dioxane, mixtures thereof and the like The amount of the two alkoxyalkanols in the aggregate employed as reactants in the process of this invention is at least 1 mole of the alkoxyalkanol mixture per mole of cyclic phosphonitrilic halide employed In addition, the amount of fluoroalkanol employed as a reactant is at least 1 mole of the fluoroalkanol per mole of cyclic phosphonitrilic halide. Thus, the stoichiometry requires, for each mole of octahalocyclotetraphosphazene reacted, between 1 mole and 7 moles of alkoxyalkanol in the aggregate and between 7 moles and 1 mole of the fluoroalkanol, the total of the alkoxyalkanols and the fluoroalkanol being 8 moles. Similarly, the stoichiometry requires, for each mole of hexahalocyclotriphosphazene, a total of 6 moles of the alkoxyalkanols and the fluoroalkanol, at least 1 mole of each type.

In carrying out the process of this invention, the phosphonitrilic halide may be added to a solution of the alkoxides in a suitable solvent of the type described above.

The order of addition of the reactants is not critical with respect to the completeness of substitution. Thus, either the alkali metal alkoxyalkyloxides, i.e., R'M and R"M, or the alkali metal fluoroalkoxide, i.e., RM, may be reacted with the phosphonitrilic halide first, or all of the oxides may be reacted with the halide simultaneously to effect complete substitution. However, the order of addition does affect the composition and physical properties of the final product and the relative proportions of alkoxy and fluoroalkoxy-substitution. Any order of addition that gives a random pattern of substitution is satisfactory. The procedure outlined above and set forth in the Example which follows was chosen to assure 1) random substitution, 2) complete replacement of halide, and 3) mild reaction conditions. Sequential additon of individual nucleophiles favors non-random substitution and should b avoided when seeking to make a solids-free fluid.

The reaction is performed at temperatures in the range between about 0° C. and about 180° C., and preferably in the range between about 25° C. and about 75° C. The reaction time will vary with the reactants employed and the temperature employed, but complete reaction can generally be obtained in between about 2 and about 24 hours. Pressure conditions during the reaction are not critical. Generally, atmospheric pressure is employed, but higher or lower pressures may be employed if desired.

The following Example illustrates a preferred embodiment of the invention and is not intended to limit the scope of this invention in any way.

EXAMPLE

To a dry 3-1 4-neck round bottom flask was added 178.2g of trifluoroethanol (1.78 mol), 100.6g of 2-methoxyethanol (1.32 mol), 120.2g of 1-methoxy-2-propanol (1.33 mol) and 1355g of tetrahydrofuran (uninhibited). Sodium metal (99.8g, 4.34g atoms) was added to the alcohols over 3.5 hrs at 10–20° C. The contents of the 3-1 flask were allowed to warm slowly to ambient temperature, and the mixture was then stirred for 24 hrs at 60° C. to complete the reaction of the sodium metal.

To a 4-neck 5-1 flask was added 601 g of cyclohexane and 301 g (0.866 mol) of hexachlorocyclotriphosphazene. The alkoxide solution prepared above was added to the contents of the 5-1 flask over 2.0 hrs at 21–67° C. The reaction mixture was stirred 1 hr at 60° C. A tetrahydrofuran solution of sodium trifluoroethoxide (3.32 meq/g, 415.0 g, 1378 meq) was then added over 3 minutes at 36–55° C. The reaction mixture was allowed to stir at ambient temperature for 2 hrs. Concentrated sulfuric acid (27.2g) was added to the reaction mixture followed by 988 g of deionized water. The reaction mixture was transferred to a 4-1 separatory funnel and the lower aqueous phase (1313 g) was removed. The organic phase was washed with deionized water (2×1000 g), and the recovered organic phase (2331 g) was dried over 70.6g of 5Å sieves overnight.

The mixture was gravity filtered through paper and the volatiles removed from the clear filtrate on a rotary evaporator. The last traces of volatiles were removed from this material by holding it at 73° C. for 1 hr on the rotary evaporator at a pressure of about 0.5 torr. The 572.3 g (97% yield) of very pale yellow liquid that was obtained was filtered through paper. The following analyses were obtained for the product:

Pour point = −42° C.
Viscosity@40° C. = 18.4 cst
Viscosity@100° C. = 3.11 cst
Density at 20° C. = 1.391 g/ml
Flashpoint > 200° C.
Average Molecular Weight by GC/MS = 672

Proton NMR indicated a substituent distribution of 51.2 mole% $OCH_2CF_3$, 26.0 mole% of $OCH_2CH_2OCH_3$, and 22.8 mole% $OCH(CH_3)CH_2OCH_3$. The average molecular weight based on this substituent distribution is 678. The liquid remained fluid and free of solids after storage for one month in a freezer at −30° C.

For comparison, a candidate hydraulic fluid was similarly prepared from hexachlorocyclotriphosphazene, trifluoroethoxide and a single alkoxyalkyloxide, i.e. 2-methoxyethoxide, in a molar ratio of 0.80/1.0, respectively. The resulting liquid completely solidified within 2 days storage at temperatures between −10° C. and −30° C.

We claim

1. A hydraulic fluid having a pour point as low as about −42° C., a flash point higher than about 200° C., and which remains substantially solids-free at temperatures as low as about −30° C., which hydraulic fluid comprises a cyclic phosphazene oligomer mixture, the structural formula of each molecule of which contains 3 or 4 units selected at random from the group consisting of

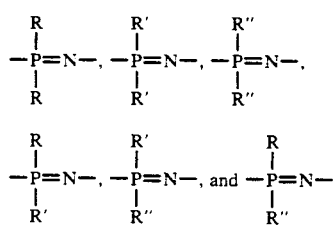

wherein R is a fluoroalkoxy group $-OCH_2(CF_2)_mCF_2Z$, where Z is hydrogen or fluorine, and m is 0 or an integer from 1 to 10; R' and R" are different alkoxyalkyloxy groups in which linear or branched $C_{1-12}$ alkoxy is substituted with linear or branched $C_{1-12}$ alkoxy; with the proviso that all of R, R' and R" are present in the oligomer mixture.

2. The hydraulic fluid of claim 1 wherein substantially all of the oligomers contain 3 units.

3. The hydraulic fluid of claim 1 wherein substantially all of the oligomers contain 4 units.

4. The hydraulic fluid of claim 1 wherein Z is fluorine and m is selected from 0, 1, 2 and 3.

5. The hydraulic fluid of claim 4 wherein m is 0.

6. The hydraulic fluid of claim 1 wherein R' is 2-methoxyethoxy.

7. The hydraulic fluid of claim 1 wherein R" is 1-methoxy-2-propoxy.

8. The hydraulic fluid of claim 1 which includes at least 1 mole of fluoroalkoxy group per mole of cyclic phosphazene oligomer.

9. The hydraulic fluid of claim 1 which includes at least 1 mole of alkoxyalkyloxy groups, in the aggregate, per mole of cyclic phosphazene oligomer.

10. The hydraulic fluid of claim 1 wherein the molar amount of R group is greater than the molar amounts of either R' and R" groups.

* * * * *